(12) United States Patent
Ohtsuka

(10) Patent No.: US 8,039,268 B2
(45) Date of Patent: Oct. 18, 2011

(54) IMMUNOCHROMATOASSAY METHOD AND IMMUNOCHROMATOASSAY KIT

(75) Inventor: Hisashi Ohtsuka, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 298 days.

(21) Appl. No.: 12/422,587

(22) Filed: Apr. 13, 2009

(65) Prior Publication Data

US 2009/0258439 A1    Oct. 15, 2009

(30) Foreign Application Priority Data

Apr. 14, 2008   (JP) ................................. 2008-104452

(51) Int. Cl.
*G01N 33/53* (2006.01)

(52) U.S. Cl. ....... 436/514; 435/7.1; 435/7.94; 435/7.92; 435/287.1; 435/287.7; 435/810; 435/975; 436/518; 436/528; 436/530; 436/808

(58) Field of Classification Search ................... 435/7.1, 435/7.94, 7.92, 287.1, 287.7, 810, 975; 436/518, 436/528, 530, 808
See application file for complete search history.

(56) References Cited

U.S. PATENT DOCUMENTS

| | | | | |
|---|---|---|---|---|
| 4,966,888 A | * | 10/1990 | Saxena et al. | 424/195.11 |
| 5,266,497 A | | 11/1993 | Imai et al. | |
| 5,779,976 A | * | 7/1998 | Leland et al. | 422/52 |
| 5,905,040 A | * | 5/1999 | Mazzara et al. | 435/320.1 |
| 5,912,257 A | * | 6/1999 | Prasad et al. | 514/356 |
| 5,935,779 A | * | 8/1999 | Massey et al. | 435/6 |
| 5,962,218 A | * | 10/1999 | Leland et al. | 435/6 |
| 6,020,208 A | * | 2/2000 | Hutchens et al. | 436/174 |
| 6,078,782 A | * | 6/2000 | Leland et al. | 435/6 |
| 6,124,137 A | * | 9/2000 | Hutchens et al. | 436/155 |
| 6,325,973 B1 | * | 12/2001 | Leland et al. | 422/52 |
| 6,402,037 B1 | * | 6/2002 | Prasad et al. | 235/487 |
| 6,511,854 B1 | * | 1/2003 | Asanov et al. | 436/518 |

FOREIGN PATENT DOCUMENTS

EP             0 582 231 A1    2/1994

* cited by examiner

*Primary Examiner* — Bao Thuy L Nguyen
(74) *Attorney, Agent, or Firm* — Sughrue Mion, PLLC

(57) ABSTRACT

An immunochromatoassay method that allows high detection sensitivity measurement. The method including the steps of: permeating an analyte solution that includes a visibly labeled second binding substance that specifically binds to a detection target substance into a test area of a chromatography medium provided with a first binding substance that specifically binds to the detection target substance, simultaneously with or after the permeation of the analyte solution into the test area, permeating a visual recognition aid solution into the chromatograph medium, the solution having a refractive index whose refractive index difference $\Delta n$ from that of the chromatograph medium is $-0.1 \leq \Delta n \leq 0.1$, and visually observing the test area while the visual recognition aid solution is permeated in the test area.

6 Claims, 4 Drawing Sheets

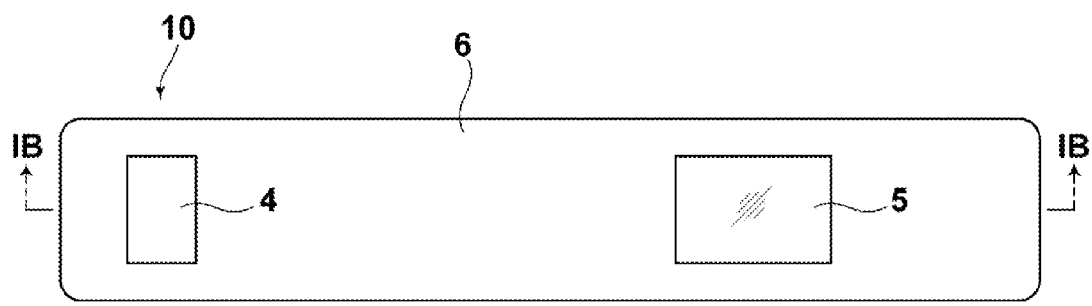
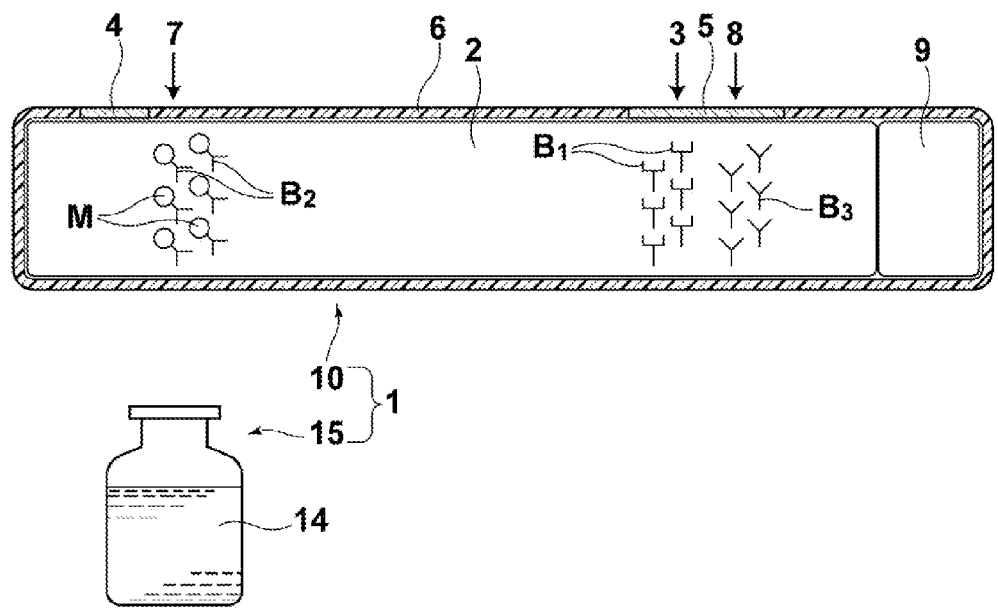

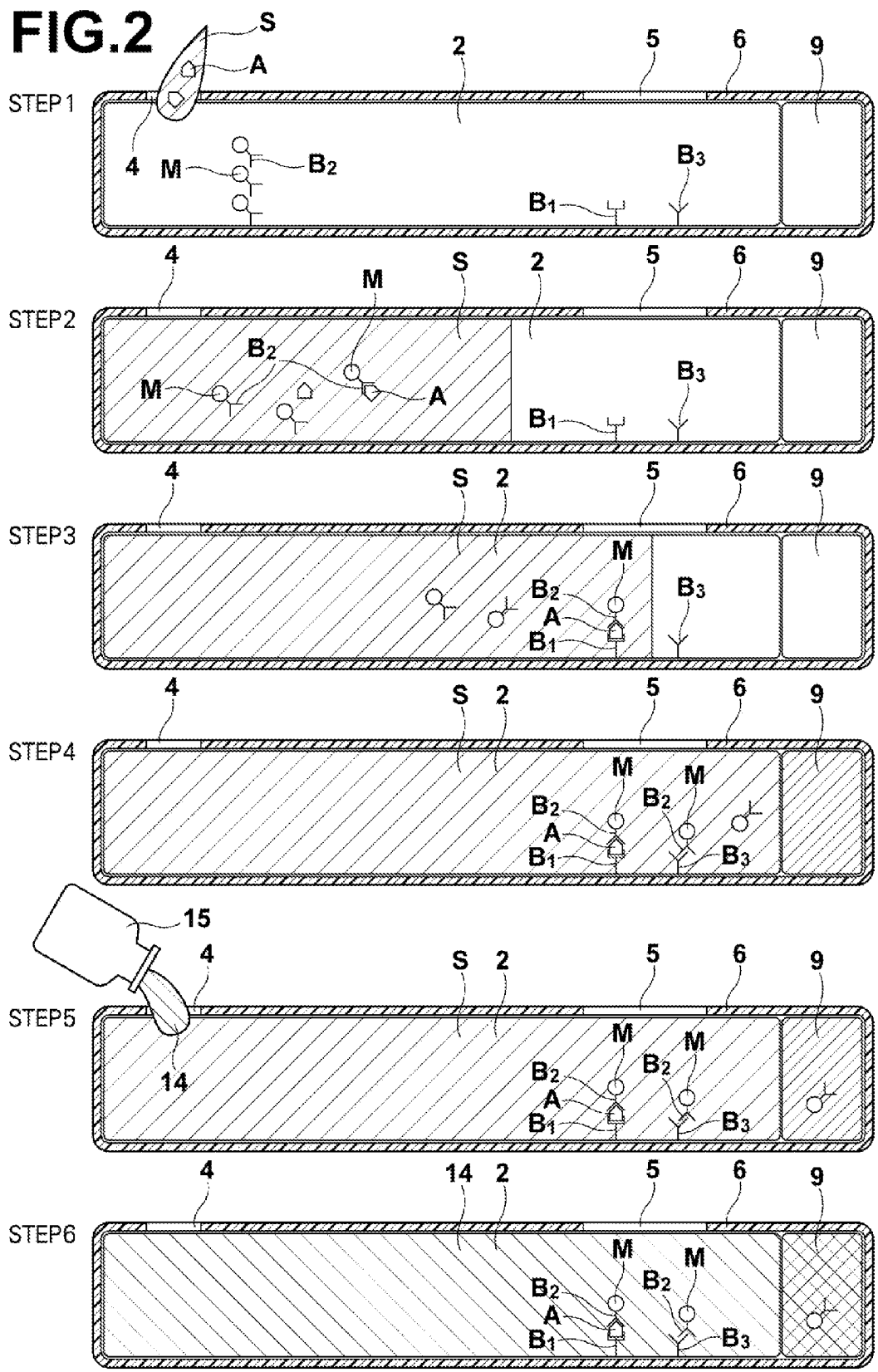

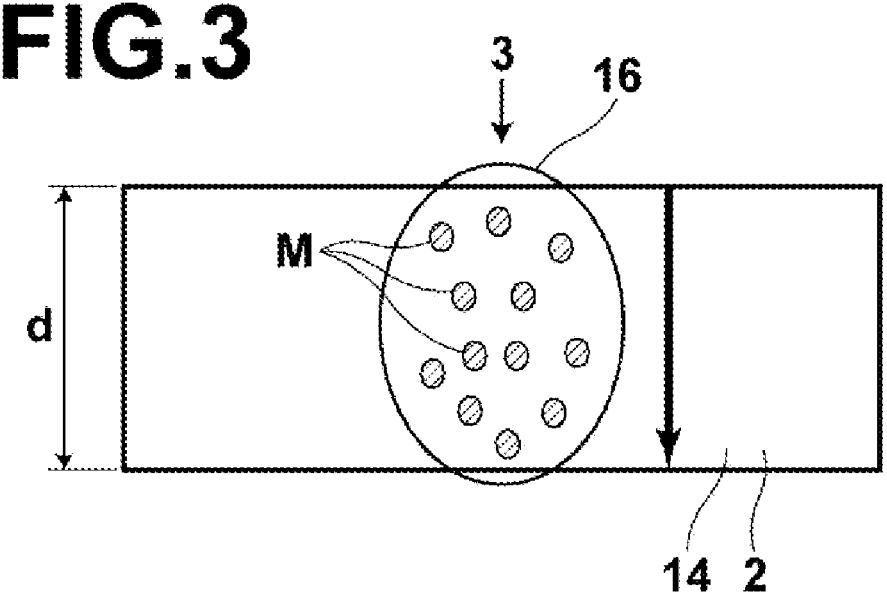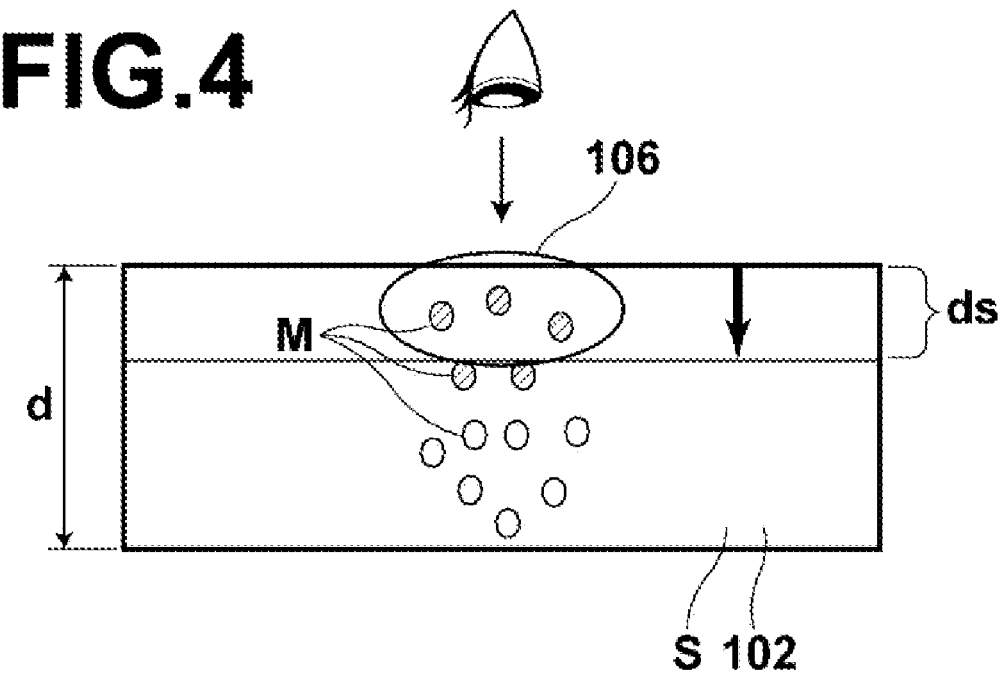

IMMUNOCHROMATOASSAY METHOD AND IMMUNOCHROMATOASSAY KIT

BACKGROUND OF THE INVENTION

1. Field of the Invention

The present invention relates to an immunochromatoassay method, one of immunoassay methods, for detecting a target substance of a particular antigen or antibody using a specific reaction between antigen and antibody, and an immunochromatoassay kit used for the immunochromatoassay method.

2. Description of the Related Art

As one of immunoassay methods for detecting a particular antigen or antibody using a specific antigen-antibody reaction, a condensation method, in which a target substance in a test sample is caused to bind by immune reaction to an antibody or antigen sensitized on particles and the state of condensation of the particles caused by the binding is measured, is generally used because it is simple and allows, in particular, visual judgment.

In the immunoassay methods, competitive reaction and sandwich reaction are widely used. As one of the so-called sandwich reaction type assays, immunochromatography is known. For example, European Patent Publication No. 0582231 proposes a preferred form of the marker particle in the immunochromatography, and U.S. Pat. No. 5,266,497 proposes an apparatus and method for a solid phase assay.

In the immunochromatography, a target substance of antigen in a test sample is typically detected by the following steps: preparing a chromatograph medium having a test area by immobilizing particles sensitized by an antibody with respect to a target substance of antigen on a chromatograph medium (e.g., membrane of nitrocellulose) as solid phase particles or by directly immobilizing the antibody on the chromatograph medium, then preparing sensitized marker particles by sensitizing particles with an antibody which is specifically bindable to the target substance, and chromatographically moving the sensitized marker particles on the chromatograph medium with the test sample.

This results in that the immobilized antibody acts as an immobilized reagent and the sensitized marker particles specifically bind to the reagent in the test area of the chromatograph medium. Then, the presence or absence of a signal or the amount thereof generated when the sensitized marker particles are captured in the test area is visually judged, whereby the presence or absence of the target substance in the test sample or the amount thereof is measured. As for the particle for preparing the marker particle, a particle of colloidal metal, such as gold, platinum, copper, or ferric oxide, a particle of colloidal metal oxide, a particle of colloidal non-metal substance, such as sulfur, or a dye particle is used.

As for the chromatograph medium, a membrane of organic macromolecule, such as nitrocellulose, having a comparatively high refractive index with a thickness of about 1 mm is generally used.

Generally, as shown in FIG. 4, the presence or absence of a signal (marker particles M) or the amount thereof is visually judged from above the thickness direction. In this case, a large difference in refractive index between membrane 102 (with refractive index=1.48) and solvent S (e.g., water, with refractive index=1.33) filled in the voids of the membrane causes the interface between them to be opaque due to light scattering. Consequently, even though the marker particles M are distributed over the entire region "d" in the thickness direction, only shaded marker particles M in region 106 adjacent to the surface (depth "ds" from the surface) are visually observed. If visual observation is performed after dropping an analyte solution and the solvent is dried, the refractive index difference between the membrane and air (refractive index=1) is further increased, causing more light scattering than when water is present in the voids and allowing only a shallower region to be visually recognized.

Where only a small number of antigens are present in the analyte solution, the number of antigens adsorbed adjacent to the surface is limited, so that an accurate visual judgment is difficult, thereby causing a problem that high detection sensitivity can not be obtained.

The present invention has been developed in view of the circumstances described above, and it is an object of the present invention to provide an immunochromatoassay method that allows an excellent visual judgment and highly sensitive detection. It is a further object of the present invention to provide an immunochromatoassay kit for implementing the immunochromatoassay method.

SUMMARY OF THE INVENTION

An immunochromatoassay method of the present invention is a method for detecting the presence or absence of a detection target substance in an analyte solution, including the steps of:

permeating the analyte solution that includes a visibly labeled second binding substance that specifically binds to the detection target substance into a test area of a chromatography medium provided with a first binding substance that specifically binds to the detection target substance;

simultaneously with or after the permeation of the analyte solution into the test area, permeating a visual recognition aid solution into the chromatograph medium, the solution having a refractive index whose refractive index difference $\Delta n$ from that of the chromatograph medium is $-0.1 \leq \Delta n \leq 0.1$; and visually observing the test area while the visual recognition aid solution is permeated in the test area.

Preferably, the refractive index difference $\Delta n$ is $-0.07 \leq \Delta n \leq 0.07$ and more preferably $-0.02 \leq \Delta n \leq 0.02$.

As for the visual recognition aid solution, a dimethylsulfoxide solution, glycerin and its aqueous solution, benzene, and paraffin oil are preferably used. Among them, the dimethylsulfoxide solution is particularly preferable.

An immunochromatoassay kit of the present invention is a kit, including:

an analyte holder which includes a chromatograph medium, a first binding substance, added to a test area of the chromatograph medium, that specifically binds to a detection target substance, a case enclosing the chromatograph medium and having an inlet for introducing an analyte solution into the chromatograph medium and a window for visually observing the test area, and a visibly labeled second binding substance, added to a portion of the chromatograph medium extending from the inlet to the test area, that specifically binds to the detection target substance; and a visual recognition aid solution to be permeated into the test area before visually observing an reaction in the test area, the solution having a refractive index whose refractive index difference $\Delta n$ from that of the chromatograph medium is $-0.1 \leq \Delta n \leq 0.1$.

Preferably, the refractive index difference $\Delta n$ is $-0.07 \leq \Delta n \leq 0.07$ and more preferably $-0.02 \leq \Delta n \leq 0.02$.

As for the visual recognition aid solution, a dimethylsulfoxide solution, glycerin and its aqueous solution, benzene, and paraffin oil are preferably used. Among them, the dimethylsulfoxide solution is particularly preferable.

According to the immunochromatoassay method of the present invention, an analyte solution is permeated into a test area and at the same time or after the permeation of the analyte solution, a visual recognition aid solution, having a refractive index whose refractive index difference Δn from that of the chromatograph medium is −0.1≦Δn≦0.1, is permeated into the chromatograph medium, and the test area is visually observed while the visual recognition aid solution is permeated in the test area. This may sufficiently reduce light scattering at the interface between the chromatograph medium and solution for visual observation because the refractive index difference between them is very small, so that the visually observable range in the depth direction of the chromatograph medium is extended. Consequently, the method allows excellent visual judgment and high detection sensitivity measurement.

The use of the immunochromatoassay kit of the present invention enables implementation of the immunochromatoassay method of the present invention, whereby excellent visual judgment and high detection sensitivity measurement may be made.

BRIEF DESCRIPTION OF THE DRAWINGS

FIGS. 1A and 1B are diagrams of an immunochromatoassay kit according to an embodiment of the present invention, illustrating a schematic structure thereof.

FIG. 2 illustrates the steps of an immunochromatoassay method according to an embodiment of the present invention.

FIG. 3 illustrates a visual inspection state in the embodiment.

FIG. 4 illustrates a visual observation state in a conventional example.

DESCRIPTION OF THE PREFERRED EMBODIMENTS

Figure 5:
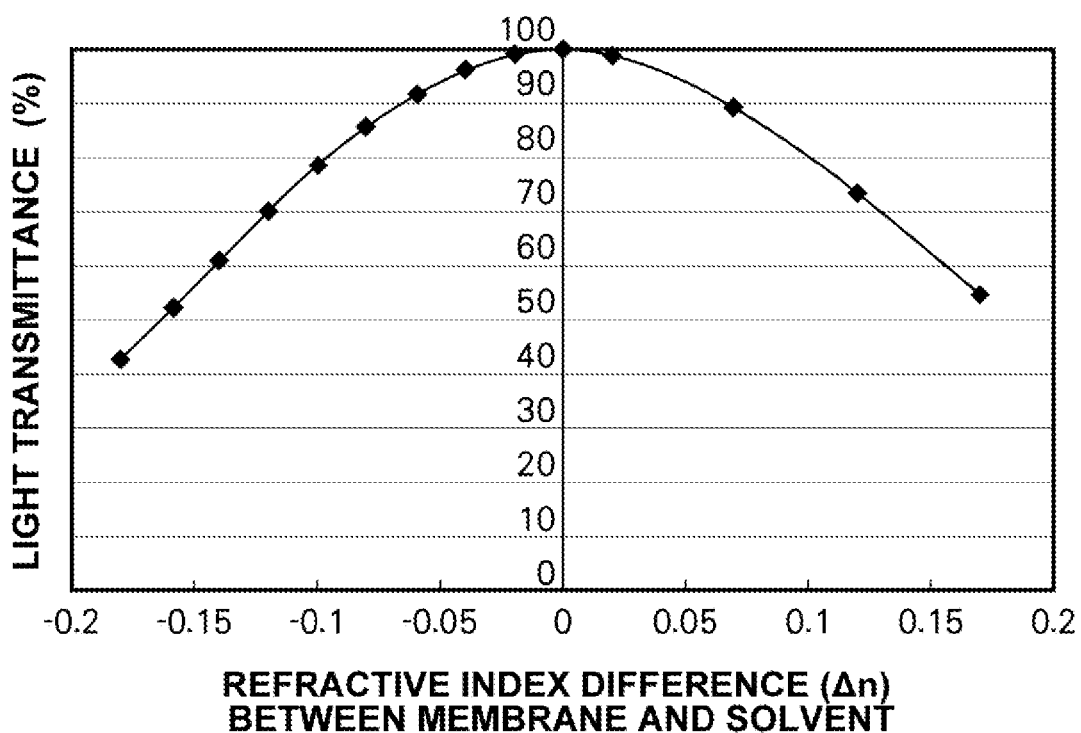
FIG. 5 illustrates dependency of the light transmittance of a membrane on the refractive index difference between the membrane and solvent.

Hereinafter, an immunochromatoassay method and an immunochromatoassay kit according to an embodiment of the present invention will be described. FIG. 1A is a plan view of an analyte holder of the immunochromatoassay kit, and FIG. 1B is a side cross-sectional view of the analyte holder, illustrating a schematic structure thereof.

Immunochromatoassay kit 1 has analyte holder 10 and ample 15. Analyte holder 10 includes chromatograph medium 2, a first binding substance $B_1$, added to test area 3 of chromatograph medium 2, that specifically binds to a detection target substance A, case 6 enclosing chromatograph medium 2 and having inlet 4 for introducing analyte solution S into chromatograph medium 2, which opens at least at the time of introducing the analyte solution, and window 5, made of a transparent material, for visually observing test area 3, and a visibly labeled second binding substance $B_2$, added to partial area 7 of chromatograph medium 2 extending from a portion corresponding to inlet 4 to test area 3, that specifically binds to detection target substance A. Ample 15 contains visual recognition aid solution 14, having a refractive index whose refractive index difference Δn from that of chromatograph medium 2 is −0.1≦Δn≦0.1, to be permeated before visually observing a reaction in test area 3.

Here, chromatograph medium 2 is formed of a membrane of nitrocellulose and enclosed in case 6 such that test area 3 is visually observable from window 5 of case 6. In the present embodiment, detection target substance A is a predetermined antigen and primary antibody $B_1$ is added to test area 3 of chromatograph medium 2 as a first binding substance that specifically binds to the detection target substance of predetermined antigen A. Further, labeled secondary antibody $B_2$ labeled by gold particles M is added to partial area 7 of membrane 2 extending from a portion corresponding to inlet 4 to test area 3 as a visibly labeled second binding substance that specifically binds to predetermined antigen A. Primary antibody $B_1$ and secondary antibody $B_2$ bind to different regions of the detection target substance of antigen A.

Further, test completion confirmation area 8 added with reference antibody $B_3$ that binds to primary antibody $B_1$ is provided downstream of test area 3 of membrane 2. Test completion confirmation area 8 is also visible from window 5 of case 6. In addition, liquid absorption pad 9 is provided at the downstream end of case 6 that absorbs analyte solution S so as not to flow back.

Here, gold particles M are used as the labeling substance for labeling the secondary antibody, but any substance may be used as long as it is visually recognizable, such as colored latex or enzyme.

Primary antibody $B_1$, secondary antibody $B_2$, and reference antibody $B_3$ are added to predetermined areas of membrane 2 respectively, and they may be simply added to the respective areas. Preferably, however, secondary antibody $B_2$ and reference antibody $B_3$ are immobilized in the respective areas of membrane 2 by amino linkage or the like, because if they are carried away by permeation movement of the analyte solution or visual recognition aid solution in the membrane, the reaction result may not be visually observed.

As for visual recognition aid solution 14 having a refractive index whose refractive index difference Δn from that of membrane 2 is −0.1≦Δn≦0.1, for example, a dimethylsulfoxide solution having a refractive index (1.46) identical to the refractive index (1.48) of nitrocellulose is preferably used (the term "identical" as used herein refers to a range in which refractive index difference Δn is, −0.02≦Δn≦0.02). Visual recognition aid solution 14 is not limited to the dimethylsulfoxide solution, and it may be any solution whose refractive index difference Δn from the refractive index of membrane 2 is −0.1≦Δn≦0.1 and does not influence antigen-antibody binding state. For example, an oil solution or a refractive index adjusted solution by controlling salt concentration in the solvent may be used.

An immunochromatoassay process flow for determining whether or not predetermined antigen A is present in an analyte solution using immunochromatoassay kit 1 according to the embodiment of the present invention will now be described.

FIG. 2 schematically illustrates the steps of the immunochromatoassay method. In order to facilitate understanding of the movement of the antigen and labeled secondary antibody, and binding state thereof with the primary antibody or reference antibody in the membrane, only one or several of them are schematically illustrated in FIG. 2.

The analyte solution is, for example, blood, urine, or snot which is the target solution for testing whether or not a target substance is contained therein.

Step 1: Test target analyte solution S is dropped from inlet 4. Here, the description will be made of a case in which analyte solution S contains the detection target substance of antigens A.

Step 2: Analyte solution S permeates and moves in membrane 2 by capillary action, then antigen A in analyte solution S binds to labeled secondary antibody $B_2$ added to membrane 2 adjacent to inlet 4, and permeates and moves in membrane 2 toward test area 3. Here, labeled secondary antibody $B_2$ not binding to antigen A is also carried toward test area 3.

Step 3: Analyte solution S moves gradually to test area 3 along membrane 2 and antigen A binding to labeled secondary antibody $B_2$ binds to primary antibody $B_1$ immobilized in test area 3, whereby a so-called sandwich is formed in which antigen A is sandwiched by primary antibody $B_1$ and labeled secondary antibody $B_2$.

Step 4: Further, labeled secondary antibody $B_2$ not binding to antigen A binds to reference antibody $B_3$. When labeled secondary antibody $B_2$ binds to reference antibody $B_3$, a red color from a gold particle is visually observed in test completion confirmation area 8, whereby it can be confirmed that the analyte solution has definitely flowed to the test area and confirmation area.

Step 5: Visual recognition aid solution 14 is introduced from inlet 4.

Step 6: Visual recognition aid solution 14 permeates and moves downstream along membrane 2 by capillary action and analyte solution S is moved to the absorption pad, whereby membrane 2 is filled with visual recognition aid solution 14 by replacing analyte solution S.

If the result of immune reaction is visually observed from window 5 under such state, the entire region of membrane 2 in the thickness direction can be visually observed, because the refractive index difference between membrane 2 and solution for visual observation is very small and light scattering at the interface between them is reduced, whereby the sensitivity is improved.

Use of a dimethylsulfoxide solution as visual recognition aid solution 14 may provide an advantageous effect of washing out labeled secondary antibodies nonspecifically adsorbing to the membrane by hydrophobic bonding, because the dimethylsulfoxide solution is a bi-philic medium having hydrophilicity and hydrophobicity, whereby background noise due to nonspecific adsorption may be drastically reduced and the S/N ratio is improved.

FIG. 3 schematically illustrates a state of the present embodiment at the time of visual observation. FIG. 3 schematically illustrates only gold particles M, which are the markers of labeled secondary antibodies binding to antigens immobilized in test area 3. When test area 3 is viewed from above the thickness direction of membrane 2, membrane 2 appears transparent since the diffractive index difference between membrane 2 and solution 14 filled in the voids of membrane 2 is small in the present embodiment and light scattering is reduced. Consequently, gold particles M which are the markers of labeled secondary antibodies binding to antigens which are binding to primary antibodies in the test area are visually recognized in area 16 extending the thickness d of the membrane. This allows more excellent visual judgment and more sensitive inspection in comparison with the conventional method that allows the markers to be visually recognized only adjacent to the surface.

In immunochromatography, a filter of bundled nitrocellulose fibers (refractive index, 1.48) with a void diameter and a fiber diameter in the range from 0.1 μm to several μm is generally used as the membrane (chromatomedium). The thickness is about 1 mm, so that light scattered from a marker in the bottom layer is influenced by scattering at the fiber interface several hundreds of times before it reaches the outside. FIG. 5 shows a simulation result of the dependency of light transmittance on diffractive index difference $\Delta n$ between the membrane material and medium filled in the voids of the membrane when light scattered from a marker in the bottom layer of the membrane with 1 mm thickness transmits upward by scattered at the interface between the void and fiber several hundreds of times as described above. The graph shows that it is necessary to select a combination of membrane and visual recognition aid solution having such refractive indices so that refractive index difference $\Delta n$ is $-0.1 \leq \Delta n \leq 0.1$ for a light transmittance not less than 80%, and $-0.07 \leq \Delta n \leq 0.07$ for a light transmittance not less than 90%. Further, it has been known that the transmittance comes closer to 100% as refractive index difference $\Delta n$ becomes smaller, and at refractive index difference $\Delta n$ is $-0.02 \leq \Delta n \leq 0.02$, where the refractive index of the membrane is substantially equal to that of the solvent, excellent visibility with a transmittance of nearly 100% may be obtained.

As described above, where the medium filled in the voids of the membrane has a large refractive index difference from the membrane, such as water or air, the light transmittance becomes very low due to large influence of scattering, resulting in low sensitivity. But, as in the present invention, a light transmittance not less than 80% may be obtained if refractive index difference $\Delta n$ is $-0.1 \leq \Delta n \leq 0.1$, and a light transmittance not less than 90% may be obtained if refractive index difference $\Delta n$ is $-0.07 \leq \Delta n \leq 0.07$, which allows high sensitivity measurement.

In the embodiment described above, after antigen-antibody binding reaction, a visual recognition aid solution is introduced in membrane 2 to replace the solvents in membrane 2, but a mixed solution of analyte solution and visual recognition aid solution (prepared so as to have a refractive index whose refractive index difference $\Delta n$ from that of the membrane is $-0.1 \leq \Delta n \leq 0.1$) may be introduced to visually observe the result of reaction. Where a mixed solution of dimethylsulfoxide solution and analyte solution is used, however, an antigen-antibody binding reaction may possibly be prevented and delayed by the presence of dimethylsulfoxide. Therefore, it is more preferable to replace the solvents after the antigen-antibody binding reaction, as in the embodiment described above.

In analyte holder 10 of assay kit 1 of the present embodiment, the description has been made of a case in which a labeled secondary antibody is added to a portion of membrane 2 in advance, but the labeled secondary antibody may not be added to the membrane. In this case, the analyte solution may be introduced to cause binding between the antigen and primary antibody, then a solution containing a labeled secondary antibody may be introduced from the inlet to cause the labeled secondary antibody to bind to the antigen binding to the primary antibody. Otherwise, the solution containing a labeled secondary antibody and analyte solution may be mixed together in advance to cause the antigen in the analyte solution and labeled secondary antibody to bind together, and the mixed solution may be introduced from the inlet.

In any case, when finally confirming the reaction by visual observation, setting of the refractive index difference $\Delta n$ between membrane 2 and the solvent filled in the membrane in the range $-0.1 \leq \Delta n \leq 0.1$ may reduce light scattering due to refractive index difference between membrane 2 and solvent, and may provide transparency in the thickness direction of the membrane, thereby allowing the density of markers M in test area 3 to be visually observed reliably, so that a high sensitivity measurement may be made.

What is claimed is:
1. An immunochromatoassay method for detecting the presence or absence of a detection target substance in an analyte solution, comprising the steps of:
   permeating the analyte solution that includes a visibly labeled second binding substance that specifically binds to the detection target substance into a test area of a chromatography medium provided with a first binding substance that specifically binds to the detection target substance;

simultaneously with or after the permeation of the analyte solution into the test area, permeating a visual recognition aid solution into the chromatograph medium, the solution having a refractive index whose refractive index difference $\Delta n$ from that of the chromatograph medium is $-0.1 \leq \Delta n \leq 0.1$; and visually observing the test area while the visual recognition aid solution is permeated in the test area.

2. The immunochromatoassay method of claim 1, wherein the refractive index difference $\Delta n$ is $-0.07 \leq \Delta n \leq 0.07$.

3. The immunochromatoassay method of claim 1, wherein the visual recognition aid solution is a dimethylsulfoxide solution.

4. An immunochromatoassay kit, comprising:

an analyte holder which includes a chromatograph medium, a first binding substance, added to a test area of the chromatograph medium, that specifically binds to a detection target substance, a case enclosing the chromatograph medium and having an inlet for introducing an analyte solution into the chromatograph medium and a window for visually observing the test area, and a visibly labeled second binding substance, added to a portion of the chromatograph medium extending from the inlet to the test area, that specifically binds to the detection target substance; and a visual recognition aid solution to be permeated into the test area before visually observing an reaction in the test area, the solution having a refractive index whose refractive index difference $\Delta n$ from that of the chromatograph medium is $-0.1 \leq \Delta n \leq 0.1$.

5. The immunochromatoassay kit of claim 4, wherein the refractive index difference $\Delta n$ is $-0.07 \leq \Delta n \leq 0.07$.

6. The immunochromatoassay kit of claim 4, wherein the visual recognition aid solution is a dimethylsulfoxide solution.

* * * * *